United States Patent [19]
Goldsmith et al.

[11] Patent Number: 5,759,031
[45] Date of Patent: Jun. 2, 1998

[54] DENTAL AIR ABRASIVE AND LASER SYSTEM

[75] Inventors: Daniel S. Goldsmith; Michael P. Howell, both of Bloomfield Hills; William S. Parker, Ann Arbor, all of Mich.

[73] Assignee: American Dental Technologies, Inc., Southfield, Mich.

[21] Appl. No.: 656,783

[22] Filed: Jun. 3, 1996

Related U.S. Application Data

[62] Division of Ser. No. 283,999, Aug. 1, 1994, which is a division of Ser. No. 804,886, Dec. 6, 1991, Pat. No. 5,334,019.

[51] Int. Cl.$^6$ .................................................. A61C 1/00
[52] U.S. Cl. ........................ 433/29; 433/142; 433/88
[58] Field of Search .............................. 433/88, 101, 31, 433/142, 29, 215; 51/307; 451/87, 88, 90

[56] References Cited

U.S. PATENT DOCUMENTS

| | | | |
|---|---|---|---|
| 2,661,537 | 12/1953 | Angell | 433/88 |
| 2,696,049 | 12/1954 | Black | 433/88 |
| 3,344,524 | 10/1967 | Kulischenko | 32/58 |
| 3,971,375 | 7/1976 | Hill | 128/173 |
| 4,180,812 | 12/1979 | Kaltenbach et al. | 340/706 |
| 4,276,023 | 6/1981 | Phillips et al. | 433/85 |
| 4,482,322 | 11/1984 | Hain et al. | 433/88 |
| 4,484,893 | 11/1984 | Finn | 433/29 |
| 4,492,575 | 1/1985 | Mabille | 433/88 |
| 4,494,932 | 1/1985 | Rzenwinski | 433/88 |
| 4,522,597 | 6/1985 | Gallant | 433/88 |
| 4,634,376 | 1/1987 | Mossle et al. | 433/29 |
| 4,635,897 | 1/1987 | Gallant | 251/5 |
| 4,708,534 | 11/1987 | Gallant | 406/75 |
| 4,753,595 | 6/1988 | Schuss et al. | 433/29 |
| 4,767,404 | 8/1988 | Renton | 604/48 |
| 4,826,431 | 5/1989 | Fujimura et al. | 433/29 |
| 4,893,440 | 1/1990 | Gallant et al. | 51/436 |
| 4,901,928 | 2/1990 | Abbott et al. | 451/90 |
| 4,940,411 | 7/1990 | Vassiliadis et al. | 433/215 |
| 4,941,298 | 7/1990 | Fernwood et al. | 51/438 |
| 5,003,434 | 3/1991 | Gosner et al. | 433/29 |
| 5,055,048 | 10/1991 | Vassiliadis et al. | 433/215 |
| 5,096,418 | 3/1992 | Coss | 433/29 |
| 5,109,637 | 5/1992 | Calafut | 51/391 |
| 5,186,625 | 2/1993 | Bailey | 433/88 |

OTHER PUBLICATIONS

*Quintessence International Dental Digest*, Sep. 1981, "Abrasive Etching of the Enamel Surface," M.E. Katora et al., pp. 967–968.

(List continued on next page.)

*Primary Examiner*—Todd E. Manahan
*Attorney, Agent, or Firm*—Gifford, Krass, Groh, Sprinkle, Patmore, Anderson & Citkowski,P.C.

[57] ABSTRACT

Improvements are provided for a dental air abrasive system of the type which utilizes a compressed gas or air which creates a gas stream. Abrasive particles are introduced into the gas stream and expelled out through one end of a nozzle whereupon the abrasive laden gas stream impinges upon the target, i.e. tooth amalgam, composites, stain and/or tooth dental filling materials. The improvements include the use of two or more hoppers each containing different sized abrasive particles, which are selectively fed, either together or independently of each other, into the gas stream. Different sized abrasive particles are provided in each hopper for cutting different types of tooth structures. Other improvements include the use of fluorescent and/or colored abrasive particles to facilitate the aiming process, a laser beam, strobe, white light or other illuminating sources for aiming the abrasive stream and/or illuminating the target area as well as a disposable nozzle for hygienic reasons. Other improvements include the use of a vacuum evacuation system to minimize dusting of the abrasive particles, as well as a dam removably positioned within the patient's mouth which reflects the abrasive particles back towards the evacuation system. Still other improvements include the use of a microvalve adjacent the nozzle which, when closed, terminates gas flow through the fluid passageway in order to further minimize dusting of the abrasive particles.

1 Claim, 2 Drawing Sheets

OTHER PUBLICATIONS

*A Textbook of Operative Dentistry*, 1956, "The Use of Airbrasive," W.H. McGehee, et al., pp. 266–273.

*The Journal of the Michigan State Dental Society*, Feb. 1950, "The Airdent Unit and the Airbrasive Technic," W.R. Mann, pp. 23–28.

*The Journal of the American Dental Association*, Nov. 1951, "Analysis of Airbrasive Procedures in Dental Practice," Epstein, pp. 573–582.

*The Journal of the New Jersey State Dental Society*, Jul. 1952, "The Airdent and I," A.R. Taylor, pp. 13–14.

*Journal of Dental Research*, Aug. 1952, "Proceedings of the Thirteenth Annual Meeting," H.B. Robinson, pp. 455, 504–505.

*The Journal of the American Dental Assoc.*, Mar. 1953, "Evaluation of the Airdent Unit: Preliminary Report," Morrison, pp. 298–303.

*Journal of Dental Research*, Oct. 1954, "Proceedings of the Thirty–Second General Meeting," H.B. Robinson, pp. 637, 666.

*The Journal of the American Dental Association*, Oct. 1954, "The Effect of High Speed Burs, Diamond Instruments and Air Abrasive in Cutting Tooth Tissue," F.A. Peyton et al., pp. 426–435.

*British Dental Journal*, Dec. 7, 1954, "The Abrasive Technique," G.E. Myers, pp. 291–295.

*The Journal of the American Dental Association*, Apr. 1955, "Appln. and Revaluation of Air Abrasive Technic," R.B. Black, pp. 409–414.

*The Journal of the American Dental Association*, "Nonmechanical Cavity Preparation", Aug., 1945, Black, pp. 955–965.

*The S.S. White "Airdent" Unit* Manual, The S.S. White Dental Mfg. Co.

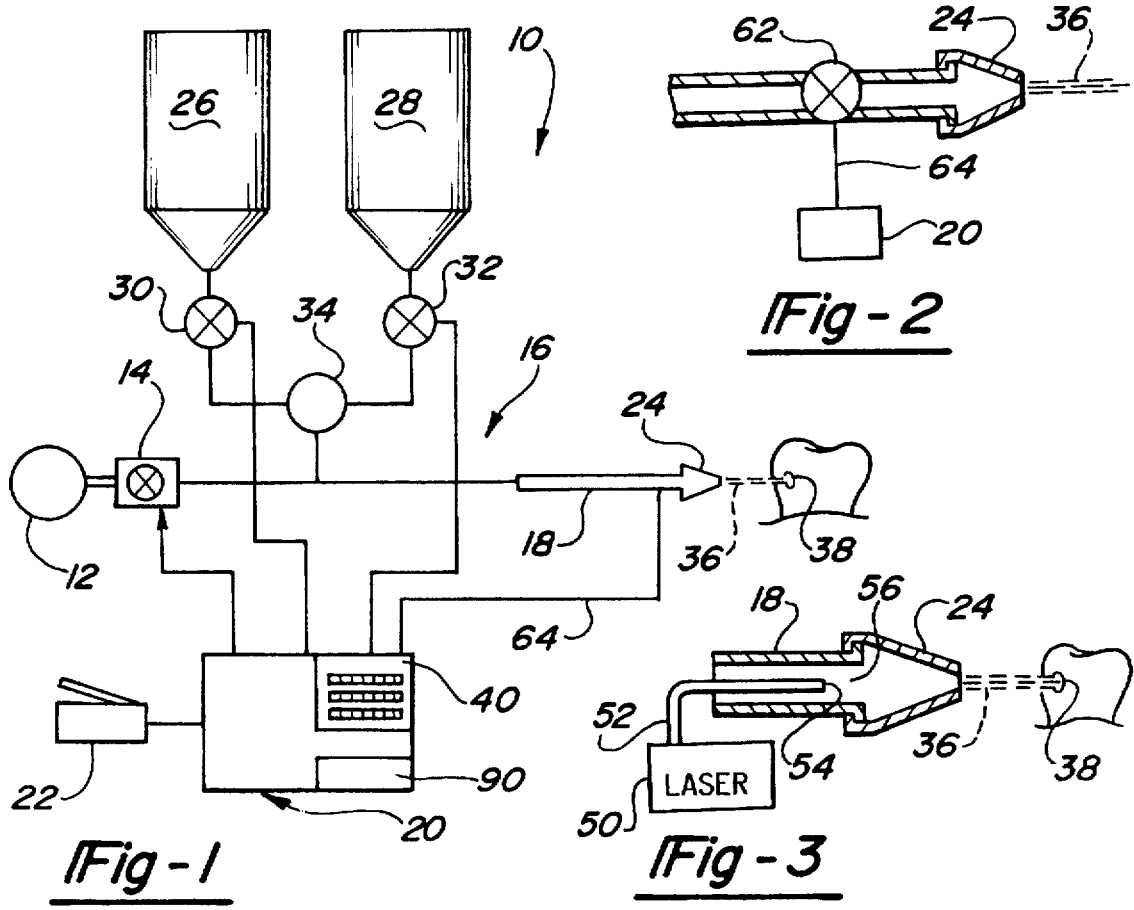
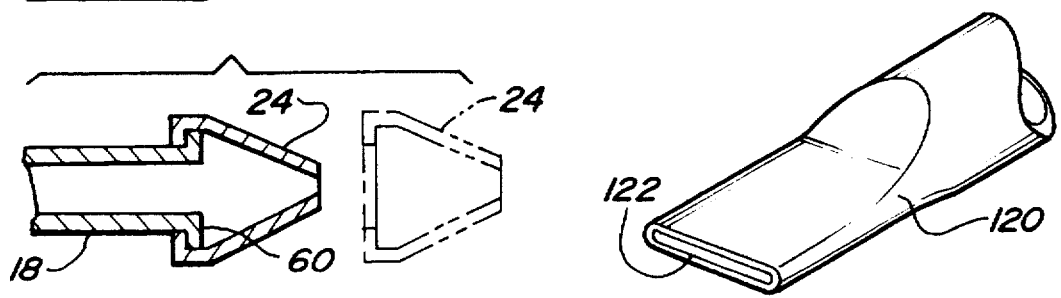
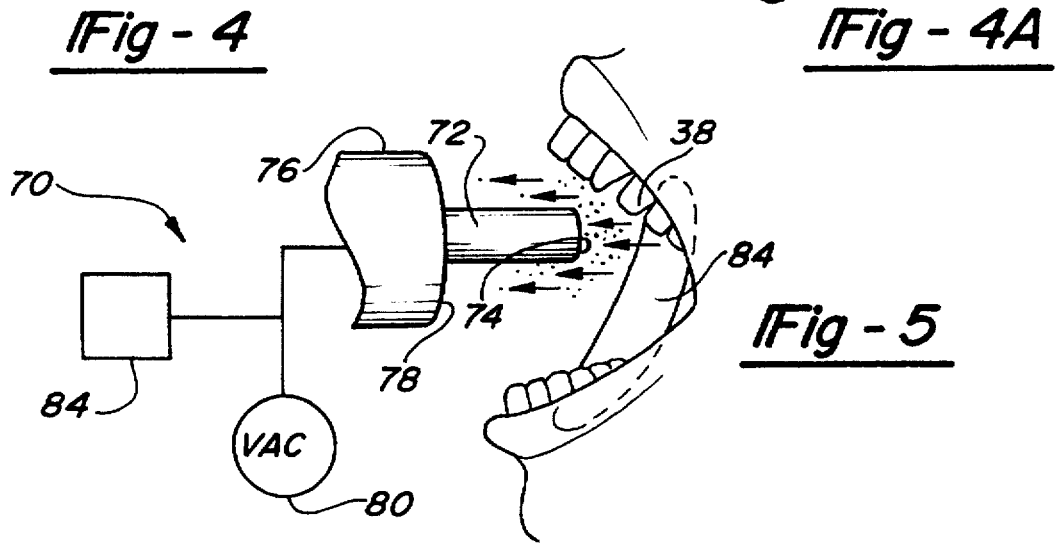

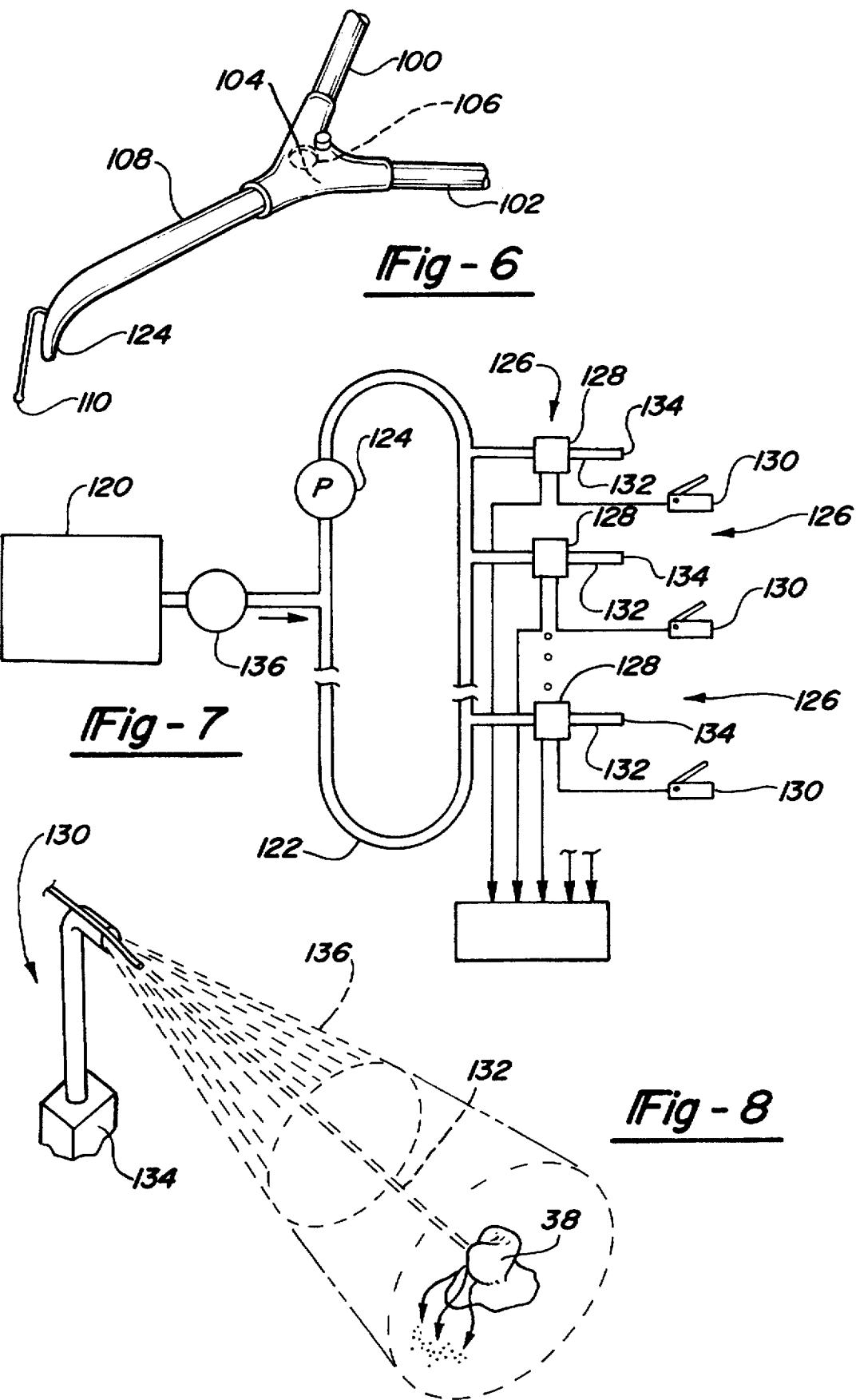

5,759,031

DENTAL AIR ABRASIVE AND LASER SYSTEM

This is a divisional of copending application Ser. No. 08/283,999 filed on Aug. 1, 1994 which is a divisional of Ser. No. 07/804,886 filed Dec. 6, 1991, now U.S. Pat. No. 5,334,019.

BACKGROUND OF THE INVENTION

1. Field of the Invention

The present invention relates generally to dental air abrasive systems for removing and/or cutting tooth structure, amalgam, composites, other dental tooth filling materials and/or stain.

2. Description of the Prior Art

There are a number of previously known air abrasive systems which have been used in dentistry for cutting tooth structure, such as enamel and dentin. These previously known air abrasive systems typically comprise an elongated tube having a nozzle at one end and having its other end coupled through a valve to a source of compressed air. Additionally, a hopper containing abrasive particles, such as aluminum oxide, are fed into the fluid passageway between the compressed air source an the nozzle. Thus, with the valve open, the compressed air creates an abrasive particle laden air stream which is expelled outwardly through the end of the nozzle. When this abrasive particle laden air stream is directed so that it impinges upon the tooth structure, cutting of the tooth structure results.

Although such dental abrasive air systems have been known for many years, they have not enjoyed widespread use or acceptance for a number of different reasons. One reason for the commercial failure of previously known dental air abrasive systems is that such systems create a "dusting" around the work area. While such abrasive particles are medically harmless, they do create an untidy and undesirable condition for the patient.

A still further disadvantage of these previously known dental air abrasive systems is that it was difficult to properly aim the effluent from the system nozzle. If improperly aimed, inadequate and imprecise cutting of the tooth structure can result or, alternatively, cutting of the wrong tooth structure and or overcutting of the tooth structure.

A still further disadvantage of these previously known dental air abrasive systems is that typically only one size of abrasive material could be fed into the air stream. In practice, however, different types of abrasive materials and/ or different sizes of abrasive materials are more desirable for different dental applications.

SUMMARY OF THE PRESENT INVENTION

The present invention provides a number of improvements in dental air abrasive systems which overcome all of the above mentioned disadvantages of the previously known devices.

In brief, the air abrasive system of the present invention comprises a source of compressed gas, preferably air, having its outlet connected to a valve. An elongated flexible tube also has one end connected to the valve and a nozzle at its opposite end. Thus, once the valve is opened, compressed air flows through the flexible tube and out through the nozzle.

At least one, and preferably two hoppers are a provided for introducing abrasive material into the gas flow stream through the flexible tube. When two hoppers are employed, different sized and/or colors and/or types of particles can be contained within each separate hopper. Then, a control system is employed to selectively introduce abrasive material from either or both of the hoppers into the gas flow stream. In doing so, the abrasive particles can be selected in dependence upon the particular dental application desired.

A number of improvements are provided for enhancing the aiming capability of the abrasive material laden gas flow stream through the nozzle and/or illumination of the target area. In one embodiment of the invention, a portion of the abrasive particles in either or both of the hoppers are made of a fluorescent or colored material. This fluorescent or colored material thus enhances the visibility of the gas flow stream and the impingement of the abrasive particles on the tooth structure for enhanced aiming capabilities.

Furthermore, as used in this patent, the term "tooth structure" includes not only the tooth but also amalgam, composites, other dental filling materials, stains, and/or other materials associated with the tooth.

In a further embodiment of the present invention, a laser beam, such as a continuous wave helium-neon laser beam has its output connected through a fiber optic cable so that the laser beam is in alignment with the discharge of the abrasive laden gas stream from the nozzle. Alternatively, a white light or a strobe light is used to illuminate the discharge from the nozzle and/or the target area to facilitate aiming the air abrasive system.

In order to minimize dusting caused by the abrasive material, a vacuum system is provided for evacuating the abrasive material after impingement of the abrasive material on the tooth structure. In the preferred embodiment, the evacuation system comprises a relatively small tube having an open end adjacent the target site. Thereafter, a larger diameter evacuation tube is positioned outside of the patient's mouth while both the large and small tubes are connected to a vacuum source. Thus, abrasive materials which escape the vacuum created by the smaller tube adjacent the target site are evacuated by the larger diameter tube outside of the patient's mouth thereby minimizing dusting of the abrasive material. Additionally, a dam is preferably removably positioned within the patient's mouth which deflects abrasive materials from the patient's mouth back towards the evacuation system which minimizes not only dusting, but also the accumulation of abrasive material within the patient's mouth.

In a further embodiment of the present invention, a fluid valve is positioned closely adjacent the nozzle at the discharge end of the tube. This valve, when closed, thus prevents the further discharge of abrasive materials out through the nozzle which also minimizes dusting of the abrasive material.

Still further improvements comprise the use of a disposable nozzle for hygienic purposes.

Still further advantages and improvements will be subsequently described.

BRIEF DESCRIPTION OF THE DRAWING

A better understanding of the present invention will be had upon reference to the following detailed description when read in conjunction with the accompanying drawings, wherein like reference characters refer to like parts throughout the several views, and in which:

FIG. 1 is a diagrammatic view illustrating a preferred embodiment of the present invention;

FIG. 2 is a partial diagrammatic view illustrating a portion of the preferred embodiment of the present invention;

FIG. 3 is a diagrammatic view illustrating still a further preferred embodiment the present invention;

FIG. 4 is a diagrammatic view illustrating the removable nozzle of the present invention;

FIG. 4A is an elevational view illustrating an alternate nozzle design;

FIG. 5 is a diagrammatic view illustrating the preferred embodiment of the evacuation system to minimize dusting;

FIG. 6 is a fragmentary view illustrating a further modification of the present invention;

FIG. 7 is a diagrammatic view illustrating yet a further embodiment of the present invention; and FIG. 8 is a fragmentary diagrammatic view illustrating a further embodiment of the present invention.

DETAILED DESCRIPTION OF A PREFERRED EMBODIMENT OF THE PRESENT INVENTION

With reference first to FIG. 1, a preferred embodiment of the air abrasive system 10 of the present invention is thereshown and comprises a pressurized gas or air source 12 having its output connected as an input to an electrically actuated valve 14. Although any compressed gas can be employed in the compressed gas source 12, preferably compressed air is used.

Although any source of compressed gas 12 can be used with the present invention, most dental offices throughout the United States and elsewhere are equipped with a source of compressed air having a pressure between 80 and 120 psi which can be used as the source 12 of compressed gas. In some applications, however, it has been found that increased pressures of about 160–200 psi are required for most efficient removal of tooth structure such as enamel and/or amalgam.

Therefore, in the preferred embodiment of the invention, a pneumatic amplifier is provided in series with the output from the compressed gas or air source 12. This pneumatic amplifier effectively increases the pressure from the source 12 to a pressure in excess of 120 psi, and preferably in the range of 160–200 psi. The actual pressure is selected by the operator or dentist in the fashion to be subsequently described.

The outlet of the valve 14 is connected to a fluid passage means 16 which includes, at its distal end, a flexible tube 18. A control system 20 controls the actuation of the valve 14 while a foot lever 22, or other actuating means, provides an input signal to the control system 20 which, in turn, opens the valve 14. With the valve 14 open, the compressed gas source 12 provides fluid flow through the fluid passageway 16 and out through a nozzle 24 at the distal end of the fluid passage means 16.

Still referring to FIG. 1, at least one, and preferably two hoppers 26 and 28 are provided for selectively introducing abrasive material into the gas flow stream through the fluid passageway 16. Preferably, the hoppers 26 and 28 are selectively connected by feed valves 30 and 32, respectively, to a mixing chamber 34. An output from the mixing chamber 34 is open to the fluid passage means 16 so that, with the valve 14 open and the mixing chamber 34 introducing abrasive material into the gas flow through the fluid passage means 16, an abrasive material laden effluent 36 is discharged out through the nozzle 24 and towards a target site 38 on the tooth structure.

The hopper feed valves 30 and 32 are preferably electric solenoid actuated valves controlled by the control system 20. The control system 20, furthermore, includes input means 40, such as a keypad, to selectively open either or both of the valves 30 and/or 32.

The use of two hoppers 26 and 28, each containing abrasive material, allows each hopper 26 and 28 to be filled with different types of abrasive materials. These different types of abrasive materials can include, for example, abrasive materials having different particle sizes, different colors or other different characteristics. For example, hopper 26 can contain abrasive material having an average size of 20–35 microns while the second hopper contains an abrasive material having a larger average size of 45–55 microns. The abrasive material is then selected through the control means 20 for different dental applications.

Alternatively, three or even more hoppers, each containing different types of abrasive materials can be used.

In addition, at least one of the abrasive materials has a majority of abrasive material particles with an average size of 45–55 microns and, preferably, in excess of 95% of this material has a particle size of between 45 and 55 microns. Preferably, the abrasive material comprises a fused white, rolled crushed aluminum oxide which has jagged edges for good cutting capability. Alternatively, the abrasive particles can be manufactured by jet milling. One or both of the hoppers can also contain a flavoring, such as a mint flavoring, to reduce any unpleasantness from the taste of the abrasive particles in the patient's mouth.

With reference now to FIGS. 1 and 6, where two hoppers 26 and 28 are used to supply different types of abrasive material to the gas or air stream, in some cases it is desirable to eliminate the mixing chamber 34 and instead introduce the abrasive material directly from the hopper 26 or 28 into the fluid passage means 16. Furthermore, in order to switch virtually instantaneously from one abrasive material in one hopper 26 to the other abrasive material in the other hopper 28, two hoses 100 and 102 form the fluid passage means 16. Furthermore, the abrasive material from one hopper 26 is introduced directly into the hose 100, while, similarly, the abrasive material from the other hopper 28 is introduced into the second hose 102.

The hoses 100 and 102 are interconnected by a Y junction 104 having an internal flapper valve 106 which opens and closes the hoses 100 and 102 in a mutually exclusive fashion. A disposable handpiece 108 having its nozzle 124 is then detachably secured to the Y junction 104.

In practice, when abrasive material from the hopper 26 is desired, the gas stream with the abrasive material from the hopper 26 is supplied through the hose 100, through the Y junction 104 and out through the handpiece 108. At the same time, the flapper valve 106 closes the second hose 102. Conversely, when abrasive material from the second hopper 28 is desired, the gas stream laden with the abrasive material from the hopper 28 is provided through the tube 102, through the junction 104 and to the disposable handpiece 108.

A primary advantage of the embodiment of the invention illustrated in FIG. 6 is that, by the use of two separate hoses 100 and 102 for the different types of abrasive materials, the dentist can virtually instantaneously change from one abrasive material to the other abrasive material as opposed to a one hose system where abrasive materials may be entrapped within the hose and must be expelled before the newly selected abrasive material is discharged from the nozzle 124. Furthermore, a single detachable and disposable handpiece 108 can be used with each patient even though different types of abrasive material are used with the same patient.

Referring to FIG. 4 and 6, the disposable handpiece 108 preferably has a nozzle 124 which is conically tapered and pointed to reduce clogging of the nozzle 124 and to reflect the deflection from a flat faced nozzle. Furthermore, either the nozzle 124 and/or the handpiece 108 should be constructed of metal which resists wear during operation of the air abrasive system.

Nozzle shapes other than conical can also be used. For example, as shown in FIG. 4A, a nozzle 120 having a rectangular outlet 122 with a length to height ratio greater than ten is particularly useful for undercutting the tooth in preparation of a dental filling. Still other shapes, such as a square nozzle outlet can also be used.

Still referring to FIG. 6, a tactile probe 110 can also be attached to the nozzle 124 which acts as a feeler probe to space the nozzle from the target area by a predetermined distance, such as 1–2 mm from the nozzle orifice. The probe 110 thus allows an optimal working distance from the target area and readily allows the dentist to detect the depth of the cut being made on the tooth structure.

In order to enhance the visibility of the effluent 36 during the cutting operation, a portion of the abrasive materials in one or both of the hoppers 26 is made of a fluorescent and/or colored material. Furthermore, although two hoppers 26 and 28 are disclosed in FIG. 1, it will be understood that alternatively, only one hopper containing one abrasive material can be mused in the air abrasive system of the present invention.

With reference now to FIG. 3, a still further means for illuminating the abrasive material laden effluent 36 and/or target area is thereshown and comprises an illumination source 50 having its output coupled by an optical fiber 52 so that the output end 54 of the optical fiber 52 is in alignment with the effluent 36 from the nozzle 24. Thus, as shown in FIG. 3, the end 54 of the optical fiber 52 is positioned within the fluid passageway 56 formed by the tube 18 adjacent the nozzle 24.

Different types of illumination means 50 can be used for aiming the effluent 36 and/or illuminating the target site. In a preferred embodiment of the invention, however, the illumination means 50 comprises a helium neon laser which provides not only an illumination means for the effluent 36 but also a means for aiming the effluent 36 at the target site 38 on the tooth structure.

Other types of illuminating means 50 can alternatively be used. These other types include, for example, a bright white light which is reflected by the abrasive particles in the effluent 36, or a strobe light to facilitate both aiming of the effluent 36 and illumination of the target site 38. Mixing a portion of abrasive material having different colors can also be used to enhance aiming of the effluent.

With reference now to FIG. 4, a preferred embodiment of the nozzle 24 is thereshown. Preferably, the nozzle 24 is detachably secured to the distal end 60 of the tube 18. Any conventional means, such as a snap fit, can be used to detachably secure the nozzle 24 to the flexible tube 18. Preferably, the nozzle 24 is disposable for hygienic reasons. Alternatively, the entire handpiece, 108 including the nozzle, is both detachable and disposable. The nozzle 124 also includes means, such as a breakaway tab, which prevents the reattachment and reuse of the nozzle 24 to thereby enhance patient safety by minimizing transmission of germs.

The present invention further provides several means for minimizing dusting of the abrasive particles during a dental therapeutic application. As best shown in FIG. 2, one preferred embodiment of the present invention utilizes a microfluid valve 62 which is provided in series with the fluid passageway 16 closely adjacent the nozzle 24. Preferably, the valve 62 is electrically actuated and is controlled by a control line 64 to the control system 20. Thus, with the valve 62 in an open position, gas flow through the fluid passageway 56 and out through the nozzle 24 as shown at 36 is established. Conversely, with the valve 62 moved to its closed position, the discharge of the abrasive material laden effluent 36 from the valve 24 is immediately terminated thereby minimizing dusting.

With reference now to FIG. 5, a preferred embodiment of an evacuation system 70 to minimize dusting is thereshown and comprises a small tube 72 having an open end 74 and a larger diameter tube 76 having an open end 78. Both of the tubes 76 and 72 are connected to a vacuum source 80 which, when actuated, inducts air flow, together with abrasive material particles, through the tubes 76 and 7.2 and to a collection bin 82.

Still referring to FIG. 5, the small tube 72 protrudes coaxially outwardly from the larger tube 76 so that the end 74 of the small tube 72 can be positioned adjacent the target site 38 in the patient's mouth. Conversely, the open end 78 of the larger tube 76 is positioned exteriorly of the patient's mouth and evacuates any materials which are reflected past the smaller tube 72 and outwardly from the patient's mouth.

Preferably, a removable dam 84 is removably positioned within the patient's mouth and is designed to reflect abrasive materials back towards the evacuation tubes 72 and 76. Thus, the dam 84 both minimizes dusting as well was the accumulation of the abrasive material within the patient's mouth. Although such abrasive material is medically harmless, it does produce an undesirable chalky taste in the patient's mouth. A flavoring, such as a mint flavoring, can also be added to the abrasive material to enhance the patient's comfort.

Dusting can also be reduced by constructing the delivery tube 18 from a flexible but inelastic material, or by providing additional structure, such as wrapping the tube 18, to minimize or eliminate its elasticity. Thus the volume of the tube 18 remains the same despite pressurization of the tube which, in turn, minimizes dusting.

With reference now to FIG. 8, a still further means is thereshown for reducing dusting of the abrasive material after impingement of the target site 38 on the tooth structure. As shown in FIG. 8, a handpiece 130 directs an abrasive material laden gas stream 132 toward the target site 38. The handpiece 130 also includes means 134 for forming a conical water spray 136 which surrounds and encloses the stream 132 at the target site 38. Thus, after impinging on the target site 38, the abrasive material forms a slurry with the water which is then evacuated from the patient's mouth by conventional liquid dental evacuators (not shown).

With reference again to FIG. 1, the control system 20 preferably includes a time delay circuit 90 which automatically terminates gas flow through the fluid passageway 16 after a predetermined time period, such as one second. Thus, following actuation or opening of the valve 14 (FIG. 1) and/or the valve 62 (FIG. 2) the time delay circuit 90 will automatically close the valve 14 and/or 62 following the predetermined time period. In order to reinitiate the gas flow through the air abrasive system, 10 the actuating means or pedal 22 must again be depressed. The delay circuit 90 thus minimizes the chance of overcutting of the tooth structure.

Although a foot lever or pedal 22 is illustrated as the means for initiating the air abrasive stream, other actuating means can alternatively be used. These other means include, for example, valve actuating means contained on the handpiece, a hand operated control panel or the like.

Still referring to FIG. 1, a dentist or other operator of the air abrasive system 10 can also use the keypad 40 on the control system 20 to input a predetermined amount of abrasive material to be released into the gas flow stream during each actuation of the pedal 22. Furthermore, the keypad 40 is used to select which hopper 26 or 28 if multiple hoppers are employed, for supplying the abrasive material to the gas flow stream. The keypad 40 can also be used to adjust the amount of abrasive material introduced into the gas flow stream during a specific time period.

The keypad 40 can also be used to adjust the pressure and/or rate of introduction of abrasive material into the gas stream in accordance with the desired rate of removal of the tooth structure.

A pressure regulator is also preferably connected in series between the source 12 of compressed gas and the valve 14. This pressure regulator is controlled by the control system 20 through the keypad 40. Thus, the operator of the air abrasive system 10 can adjust the pressure of the gas from the source introduced into the fluid passageway 16 in order to accommodate different types of dental procedures. For example, the removal of enamel may require a certain pressure, for example 120 psi, for most efficient removal while the removal of amalgam would require a different pressure, for example 150 psi, for most efficient removal.

With reference now to FIG. 7, a still further modification of the present invention is thereshown for an abrasive material laden gas stream for use with multiple work stations. As shown in FIG. 7, a main abrasive system 120 introduces an abrasive material laden gas stream into a circulating loop 122. The gas in the loop 122, together with its entrained abrasive material, is continuously recirculated throughout the loop 122 by a recirculating means 124, such as a gas pump.

At least two, and preferably more remote stations 126 are provided for delivering the gas stream at remote locations. Each remote station 126 comprises a valve 128 which is actuated at the remote station 126 by a switch 130, such as a foot lever, a switch on the handpiece or other means. When the valve 128 is opened, material from the recirculating loop 122 is discharged through delivery means 132 at the remote station and out through a nozzle 134 at the remote station to the target site. Simultaneously, the main unit 120 provides compressed gas or air with entrained abrasive material into the circulating loop 122 to replace the compressed gas and abrasive material removed from the loop 122 by the opening of the valve 128. Any conventional means, such as a feedback from the individual remote stations 126 or pressure responsive means at the main unit 120 are used to replace the withdrawn compressed gas and material from the loop 122.

Upon release of the switch 130 at the remote station, 126 each valve 128 operates as a relief valve which releases pressure from the delivery system 132 at the remote station 126 and channels the release pressure, together with its entrained abrasive material, to a collection unit.

It has also been found that the tooth structure and especially the enamel and dentin, can be desensitized or numbed by spraying the tooth structure with an unfocussed spray of the abrasive material laden gas stream. The unfocussed spray is insufficient to actually cut the tooth structure. The precise reason for this phenomenon is unknown.

From the foregoing, it can be seen that the present invention provides many improvements in dental air abrasive systems. Having described our invention, however, many modifications thereto will become apparent to those skilled in the art to which it pertains without deviation from the spirit of the invention as defined by the scope of the appended claims.

We claim:

1. An apparatus for cutting tooth structure comprising:

a source of abrasive material containing an abrasive material, means for creating a gas stream, means for delivering said gas stream to a target site at the tooth structure, means for selectively feeding abrasive material from said source of abrasive material into said gas stream upstream from said delivering means so that said gas stream is laden with abrasive material, wherein said gas stream is of sufficient velocity so that, when laden with abrasive material, cuts tooth structure at the target site, and means for illuminating the target site comprising a light source and an elongated optical transmission fiber having one end disposed adjacent the light source and a second end directed at the target site, said fiber transmitting light from said source to said target site wherein said light source has optical qualities capable of curing light curable dental composites.

* * * * *